US011202619B2

(12) United States Patent
Abe et al.

(10) Patent No.: US 11,202,619 B2
(45) Date of Patent: Dec. 21, 2021

(54) ULTRASONIC DIAGNOSTIC APPARATUS, MEDICAL IMAGE PROCESSING APPARATUS, AND MEDICAL IMAGE PROCESSING METHOD

(71) Applicant: Toshiba Medical Systems Corporation, Otawara (JP)

(72) Inventors: Yasuhiko Abe, Otawara (JP); Hiroyuki Ohuchi, Otawara (JP); Tetsuya Kawagishi, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 906 days.

(21) Appl. No.: 14/100,734

(22) Filed: Dec. 9, 2013

(65) Prior Publication Data

US 2014/0100461 A1 Apr. 10, 2014

Related U.S. Application Data

(63) Continuation of application No. PCT/JP2012/064898, filed on Jun. 11, 2012.

(30) Foreign Application Priority Data

Jun. 9, 2011 (JP) .............................. JP2011-129532

(51) Int. Cl.
*A61B 8/00* (2006.01)
*A61B 8/08* (2006.01)

(52) U.S. Cl.
CPC .......... *A61B 8/5292* (2013.01); *A61B 8/0883* (2013.01); *A61B 8/483* (2013.01); *A61B 8/5223* (2013.01)

(58) Field of Classification Search
None
See application file for complete search history.

(56) References Cited

U.S. PATENT DOCUMENTS 7,558,402 B2 7/2009 Zhou et al.
8,287,457 B2 10/2012 Salgo et al.
(Continued)

FOREIGN PATENT DOCUMENTS

CN 101116621 A 2/2008
CN 101336844 A 1/2009
(Continued)

OTHER PUBLICATIONS

Zhang et al. , "4-D Cardiac MR Image Analysis: Left and Right Ventricular Morphology and Function", IEEE Trans Med Imaging, Feb. 2010.*
Donato et al., Left ventricular geometry in normal and post-anterior myocardial infarction patients: sphericity index and 'new' conicity index comparisons, European Journal of Cardio-thoracic Surgery 29S (2006), pp. S225-S230.*

(Continued)

*Primary Examiner* — Christopher L Cook
(74) *Attorney, Agent, or Firm* — Oblon, McClelland, Maier & Neustadt, L.L.P.

(57) ABSTRACT

An ultrasonic diagnostic apparatus according to an embodiment comprises a data acquisition unit configured to execute ultrasonic scanning for a tissue region throughout a predetermined period and acquire a plurality of image data respectively corresponding to phases in the predetermined period; a positional information acquisition unit configured to acquire positional information of a region of interest in the tissue region at least one phase in the period by executing tracking processing using at least part of the plurality of image data; a shape information calculation unit configured to calculate shape information corresponding to the region of interest at least one phase in the period by using positional information of the region of interest at the at least one phase; and an output unit configured to output the shape information at the at least one phase.

18 Claims, 9 Drawing Sheets

(56) References Cited

U.S. PATENT DOCUMENTS

| | | | |
|---|---|---|---|
| 2003/0153823 A1* | 8/2003 | Geiser | G06T 7/0012 600/407 |
| 2004/0208341 A1 | 10/2004 | Zhou et al. | |
| 2007/0167777 A1* | 7/2007 | Abe | A61B 8/463 600/441 |
| 2008/0097210 A1* | 4/2008 | Salgo | A61B 8/0883 600/445 |
| 2010/0056919 A1 | 3/2010 | Abe | |
| 2010/0158332 A1 | 6/2010 | Rico et al. | |
| 2010/0195881 A1* | 8/2010 | Orderud | A61B 8/08 382/131 |
| 2010/0198071 A1 | 8/2010 | Ohuchi et al. | |

FOREIGN PATENT DOCUMENTS

| | | | |
|---|---|---|---|
| CN | 101791232 A | | 8/2010 |
| JP | 2004-313291 A | | 11/2004 |
| JP | 2009-112374 A | | 5/2009 |
| JP | 2009-226226 A | | 10/2009 |
| JP | 2010-502239 A | | 1/2010 |
| JP | 2010-51731 A | | 3/2010 |
| JP | 2010-194298 A | | 9/2010 |
| WO | WO 2007/138523 A1 | | 12/2007 |

OTHER PUBLICATIONS

Stypmann et al., "Echocardiographic assessment of global left ventricular function in mice", Laboratory Animals, 2009, vol. 43, pp. 127-137.*

Harjai et al., "Does left ventricle shape influence clinical outcome in heart failure?", 2000, Clin. Cardiol., 23, pp. 813-819.*

Folland et al., "Assessment of left ventricular ejection fraction and volumes by real time two dimensional echocardiography", Oct. 1979 (Year: 1979).*

Ayumi Nakaboh, et al. "Echocardiographic Assessment of the Relationship Between Left Ventricular Geometry and Dyssynchrony", Jpn J. Med Ultrasonics, vol. 37, No. 4. 2010, pp. 499-505 with English Abstract.

Combined Office Action and Search Report dated Jan. 15, 2015 in Chinese Patent Application No. 201280001016.3 (with English translation of categories of cited documents).

Combined Chinese Office Action and Search Report dated Mar. 25, 2014, in Chinese Patent Application No. 201280001016.3 with English translation.

International Search Report dated Aug. 14, 2012 for PCT/JP2012/064898 filed on Jun. 11, 2012 with English Translation.

International Written Opinion dated Aug. 14, 2012 for PCT/JP2012/064898 filed on Jun. 11, 2012.

* cited by examiner

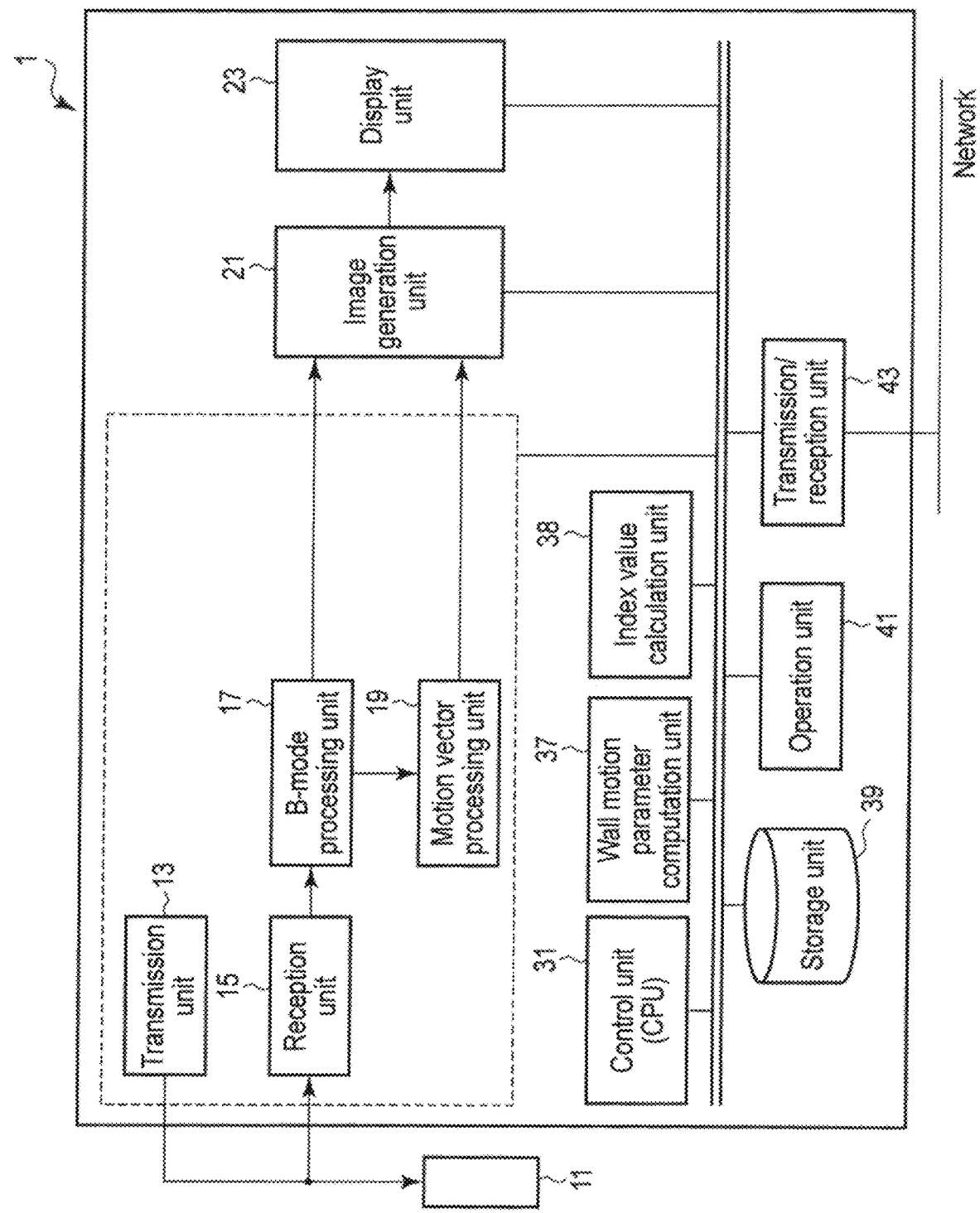
F I G. 1

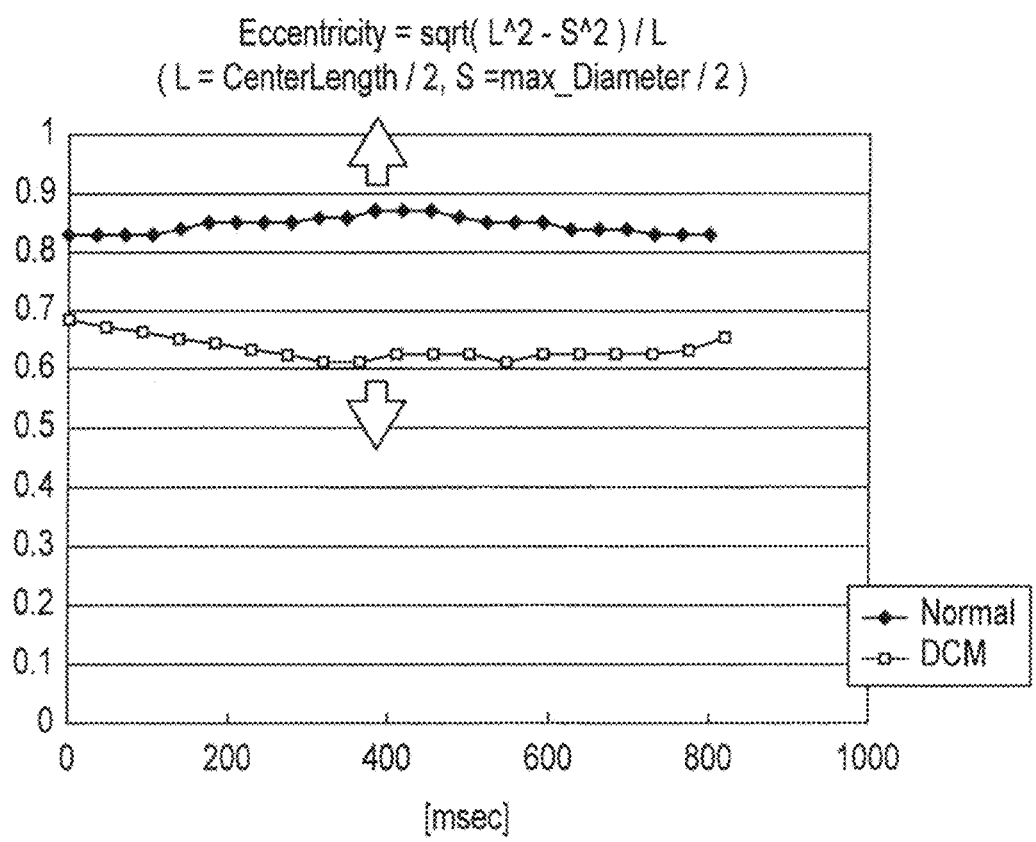
F I G. 9

Normal at ES

DCM at ES

ULTRASONIC DIAGNOSTIC APPARATUS, MEDICAL IMAGE PROCESSING APPARATUS, AND MEDICAL IMAGE PROCESSING METHOD

CROSS-REFERENCE TO RELATED APPLICATIONS

This application is based upon and claims the benefit of priority from the prior Japanese Patent Application No. 2011-129532, filed Jun. 9, 2011 the entire contents all of which are incorporated herein by reference.

BACKGROUND OF THE INVENTION

1. Field of the Invention

Embodiments described herein relate generally to an ultrasonic diagnostic apparatus, medical image processing apparatus, and medical image processing method which defines indices for determining the shape of a heart.

2. Description of the Related Art

It is known that in general, the normal left ventricle has an elongated spheroidal shape, but the left ventricle of the diseased heart is rounded to approach a sphere. A typical example of such a disease is dilated cardiomyopathy (DCM). Conventionally, there has been proposed a technique of calculating indices for determining the shape of the heart by using echocardiography and diagnosing the heart by using the indices. For example, there is a practice of acquiring a long-axis length and a short-axis diameter at a predetermined level (e.g., at a position corresponding to ⅓ the long-axis length from the valve ring) by manual measurement based on a two-dimensional apical view of the left ventricle and performing shape assessment of the left ventricle by using the ratio between the long-axis length and the short-axis radius or the like. When performing similar ratio analysis based on three-dimensional data, this technique performs measurement in the above manner upon extracting a two-dimensional apical view of the left ventricle using multiplanar reconstruction (MPR) display. There has also been proposed a technique of assessing the three-dimensional shape information of the left ventricle as an average curvature (see, for example, Jpn. PCT National Publication No. 2010-502239).

When calculating an index for determining the shape of the heart by using a conventional ultrasonic diagnostic apparatus, the operator needs to perform manual measurement. That is, this technique lacks in convenience and rapidity. In particular, it is practically difficult to analyze a time change in measured value throughout one cardiac cycle. Such a change is therefore not assessed. In addition, measurement based on three-dimensional data depends on how an MPR slice is selected, and hence measurement results are unstable. In addition, the technique typified by patent literature 1 is designed to acquire comprehensive information by surface detection, but cannot simultaneously obtain local information such as strain.

In consideration of the above problems, it is an object to provide an ultrasonic diagnostic apparatus, medical image processing apparatus, and medical image processing method which can execute index calculation for highly objective shape determination of the heart with higher rapidity and less working load than the prior art.

Solution to Problem

An ultrasonic diagnostic apparatus according to an embodiment comprises a data acquisition unit configured to execute ultrasonic scanning for a tissue region throughout a predetermined period and acquire a plurality of image data respectively corresponding to phases in the predetermined period; a positional information acquisition unit configured to acquire positional information of a region of interest in the tissue region at least one phase in the period by executing tracking processing using at least part of the plurality of image data; a shape information calculation unit configured to calculate shape information corresponding to the region of interest at least one phase in the period by using positional information of the region of interest at the at least one phase; and an output unit configured to output the shape information at the at least one phase.

BRIEF DESCRIPTION OF DRAWINGS

FIG. 1 is a block diagram showing the arrangement of an ultrasonic diagnostic apparatus 1 according to the first embodiment.

FIG. 9 is a graph showing an intra-cardiac cycle time change curve with an index value being generated as an eccentricity.

DESCRIPTION OF EMBODIMENTS

Figure 2:
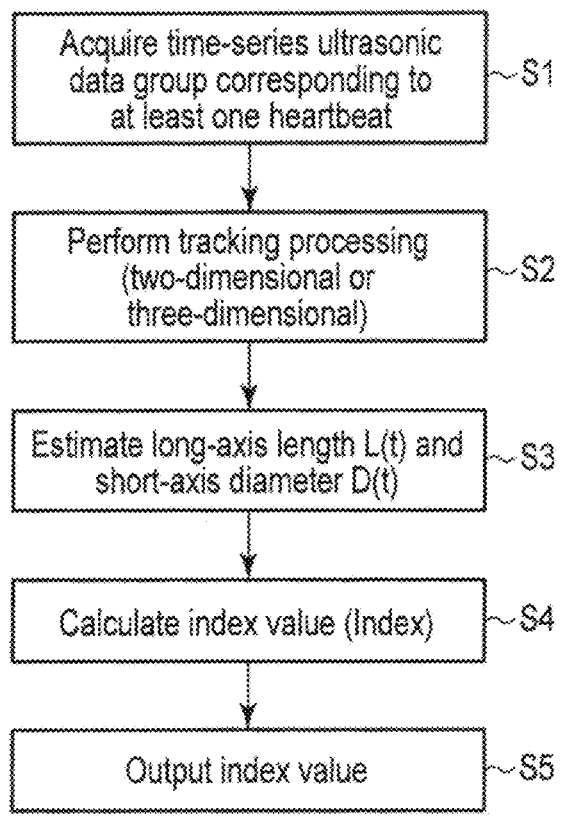
FIG. 2 is a flowchart showing a procedure for processing based on a shape information calculation function.

An embodiment will be described below with reference to the accompanying drawing. The same reference numerals denote constituent elements having almost the same functions and arrangements, and a repetitive description will be made only when required.

Note that in the following embodiment, an example of application to an ultrasonic diagnostic apparatus will be described. However, the embodiment is not limited to this, and can also be applied to medical image processing apparatuses such as a workstation and a personal computer. In addition, these ultrasonic diagnostic apparatus and medical image processing apparatus may be implemented by installing a medical image processing method for implementing a shape information calculation function (to be described later) in apparatuses.

First Embodiment

FIG. 1 is a block diagram showing the arrangement of an ultrasonic diagnostic apparatus 1 according to the first embodiment. The ultrasonic diagnostic apparatus 1 includes an ultrasonic probe 11, a transmission unit 13, a reception unit 15, a B-mode processing unit 17, a motion vector processing unit 19, an image generation unit 21, a display unit 23, a control unit (CPU) 31, a wall motion parameter computation unit 37, an index value calculation unit 38, a storage unit 39, an operation unit 41, and a network interface unit 43. Note that when the embodiment is applied to a medical image processing apparatus, the elements enclosed by the dotted line in FIG. 1 are constituent elements.

The ultrasonic probe 11 includes a plurality of piezoelectric transducers which generate ultrasonic waves based on driving signals from the transmission unit 13 and convert reflected waves from an object into electrical signals, a matching layer provided for the piezoelectric transducers, and a backing member which prevents ultrasonic waves from propagating backward from the piezoelectric transducers. When the ultrasonic probe 11 transmits ultrasonic waves to an object, various kinds of harmonic components are generated accompanying the propagation of ultrasonic waves due to the nonlinearity and the like of living body tissues. The ultrasonic probe 11 receives, as reflected waves (echoes), fundamental waves and harmonic components constituting transmission ultrasonic waves upon backward scattering such as micro-scattering at acoustic impedance boundaries of living body tissues.

The transmission unit 13 includes a delay circuit, a pulser circuit, and the like (none of which are shown). The pulser circuit repetitively generates rate pulses for the formation of transmission ultrasonic waves at a predetermined rate frequency fr Hz (period: 1/fr sec). The delay circuit gives each rate pulse a delay time necessary to focus an ultrasonic wave into a beam and determine transmission directivity for each channel. The transmission unit 13 applies a driving pulse for each transducer so as to form an ultrasonic beam toward a predetermined scanning line at the timing based on this rate pulse.

The reception unit 15 includes an amplifier circuit, A/D converter, and adder (none of which are shown). The amplifier circuit amplifies an echo signal received via the probe 11 for each channel. The A/D converter gives the amplified echo signals delay times necessary to determine reception directivity. The adder then performs addition processing. This addition generates an ultrasonic echo signal corresponding to a predetermined scanning line.

The B-mode processing unit 17 performs envelope detection processing for the ultrasonic echo signal received from the reception unit 15 to generate a B-mode signal corresponding to the amplitude intensity of the ultrasonic echo.

The motion vector processing unit 19 detects the movement position of a tissue between two ultrasonic data at different phases by using pattern matching processing (speckle tracking processing), and obtains the movement amount (or speed) of each tissue based on the movement position. More specifically, with regard to a region of interest in one ultrasonic data, the motion vector processing unit 19 obtains a corresponding region in the other ultrasonic data which has the highest similarity. Obtaining the distance between the region of interest and the corresponding region can obtain the movement amount of the tissue. In addition, dividing the movement amount by the time difference between the ultrasonic data (the frame rate or volume rate) can obtain the moving speed of the tissue. Performing this processing at each position on the ultrasonic data can acquire the displacement of each tissue (motion vector) or spatio-temporal distribution data concerning the displacements of tissues. Note that in this case, ultrasonic data is defined as a set of reception signals having two-dimensional or three-dimensional positional information (i.e., a set of reception signals having spatial information).

The image generation unit 21 generates a B-mode ultrasonic image representing a two-dimensional distribution concerning a predetermined slice of a B-mode signal. In addition, based on computed wall motion parameters, the image generation unit 21 generates a two-dimensional image or three-dimensional image by mapping the wall motion parameters by using a technique such as surface rendering or polar-mapping.

The display unit 23 displays an ultrasonic image, a wall motion parameter image with wall motion parameters being mapped at the respective corresponding positions, a time change curve of a wall motion parameter for each portion, and the like in predetermined forms based on video signals from the image generation unit 21. In addition, the display unit 23 labels each portion segmented by segmentation processing in accordance with a shape information calculation function (to be described later), and displays the resultant portions in a predetermined form.

The control unit (CPU) 31 has a function as an information processing apparatus (computer), and statically or dynamically controls the operation of this ultrasonic diagnostic apparatus body. In particular, the control unit 31 implements a shape information calculation function (to be described later) by expanding the dedicated program stored in the storage unit 39 into a memory (not shown).

The wall motion parameter computation unit 37 generates a wall motion parameter for each phase based on the spatio-temporal distribution data output from the motion vector processing unit 19. In this case, wall motion parameters are physical information which can be acquired in association with information about tissue motion such as a displacement, strain, strain rate, velocity, twist, and twist rate in a predetermined direction of a predetermined tissue such as a cardiac wall.

The index value calculation unit 38 calculates a shape index indicating the shape of a target tissue region in accordance with the shape information calculation function (to be described later), and also generates shape information defined by using the shape index.

The storage unit 39 includes recording media such as magnetic disks (floppy® disks, hard disks, and the like), optical disks (CD-ROMs, DVDs, and the like), and semiconductor memories and a device which reads out information recorded on these media. The storage unit 37 stores transmission/reception conditions, a predetermined scan sequence, raw data corresponding to each phase, ultrasonic image data (e.g., tissue image data captured in a tissue Doppler mode, B mode, or the like), ultrasonic data generated in advance for each phase, spatio-temporal distribution data associated with motion vectors, a program for implementing the shape information calculation function (to be described later), diagnostic information (patient ID, findings by doctors, and the like), a diagnostic protocol, a body mark generation program, and the like.

The operation unit 41 is connected to the apparatus main body and includes a mouse, trackball, mode switch, and keyboard which are used to, for example, issue various kinds of instructions from the operator, an instruction to set a region of interest (ROI), and instructions to set various kinds of image quality conditions and to select arbitrary wall motion parameters, arbitrary analysis periods, and cardiac phases in the shape information calculation function (to be described later).

The network interface unit 43 is a device for transmitting/receiving information to/from other apparatuses via a network. The network interface unit 43 can transfer data such as ultrasonic images obtained by the ultrasonic diagnostic apparatus 1, analysis results, and the like to other apparatuses via the network.

(Shape Information Calculation Function)

The shape information calculation function of the ultrasonic diagnostic apparatus 1 will be described next. This function automatically calculates, as the shape of a tissue (e.g., the left ventricle of the heart) which periodically moves, shape information by using the positional information of the tissue obtained by tracking processing throughout at least one cycle, and outputs the information in a predetermined form. In this case, shape information means direct information concerning a shape, e.g., a long-axis length L and a short-axis diameter D (e.g., a diameter or radius) of a diagnostic target, an index value (shape index value) reflecting the shape of the moving tissue which is obtained by using the long-axis length L and short-axis diameter D of the diagnostic target, or statistical information, e.g., the average value, maximum value, minimum value, median value, or standard deviation, of the short-axis diameters D. For the sake of a concrete description, the following will exemplify a case in which a diagnostic target is the left ventricle of the heart, and the shape index value obtained based on the long-axis length L and short-axis diameter D of the left ventricle is output as shape information. However, the target of this shape information calculation function is not limited to the left ventricle of the heart, and may be the right atrium, the left atrium, the right ventricle, or the heart of a fetus, or may be a blood vessel (carotid artery), hepatic tumor, mammary gland tumor, or the like.

FIG. 2 is a flowchart showing a procedure for processing based on this shape information calculation function. The contents of processing executed in each step will be described below.

[Acquisition of Time-Series Volume Data Group throughout Predetermined Period: Step S1]

First of all, the apparatus acquires time-series ultrasonic data throughout a predetermined period corresponding to at least one heartbeat (to be referred to as a "time-series ultrasonic data group" hereinafter) with a region to be scanned (two-dimensional or three-dimensional region) including at least the left ventricle of an object (step S1).

[Tracking Processing: Step S2]

The motion vector processing unit 19 then extracts a myocardial portion in a region of interest in ultrasonic data, of the ultrasonic data corresponding to each phase in one or more heartbeats of the time-series ultrasonic data group acquired throughout the predetermined period, which corresponds to a predetermined phase based on an instruction from the user, and executes speckle tracking processing of temporally tracking the extracted local myocardial portion by two-dimensional or three-dimensional pattern matching processing, thereby computing spatio-temporal motion vector information (step S2).

The wall motion parameter computation unit 37 computes wall motion parameters typified by the wall motion parameters (e.g., strain, strain rate, displacement, velocity, twist, and twist rate) and the like selected by the operator via the operation unit 41 by using computed spatio-temporal motion vector information, and generates a two-dimensional or three-dimensional wall motion parameter group constituted by wall motion parameters corresponding to one or more heartbeats.

[Estimation of Long-Axis Length L and Short-Axis Diameter D: Step S3]

The index value calculation unit 38 then estimates a long-axis L(t) and short-axis diameter D(t) at each phase (step S3). The long-axis length L(t) and the short-axis diameter D(t) can be defined as follows.

(Long-Axis Length L(t))

Assume that when a region to be scanned is a two-dimensional region, the long-axis length is the distance between the cardiac apex position and the middle point of a straight line connecting the edge of basal myocardium on an apical view at a predetermined phase (initial phase). Assume also that when a region to be scanned is a three-dimensional region, the long-axis length is the distance between the cardiac apex position and the barycenter of the short-axis C-mode as curved surface of the edge of basal level. In this case, the cardiac apex position indicates the distance from the middle point of a straight line connecting the edge of basal myocardium to the furthest position on a contour at an end-diastole (ED). At other phases, the cardiac apex position indicates the furthest position on a contour from the middle point of a straight line connecting the edge of basal myocardium as in the case of an end-diastole (ED) or a position set by tracking the cardiac apex point at an end-diastole. In addition, when a region to be scanned is either a two-dimensional region or a three-dimensional region, the position of the edge of basal level means the average position of a annulus portion of a contour.

(Short-Axis Diameter D(t))

Figure 3:
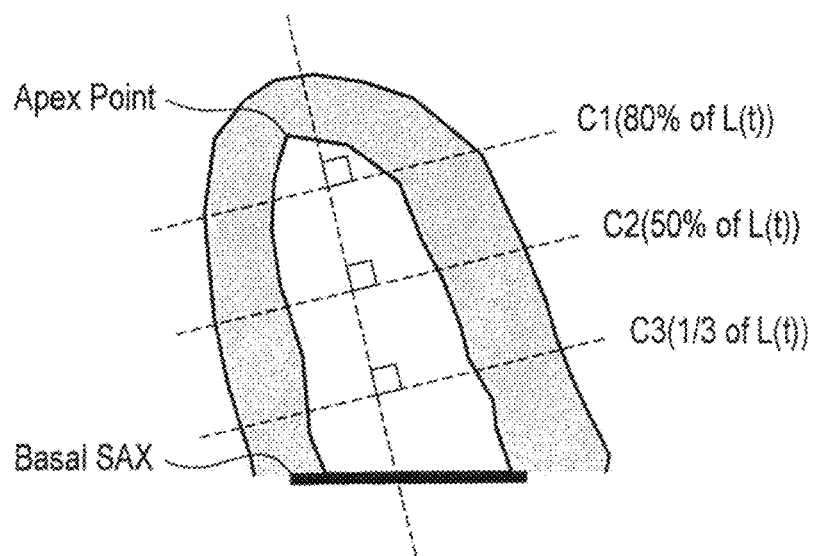
FIG. 3 is a schematic figure of an apical view showing short-axis surface positions at predetermined levels along the long-axis length.

Assume that when a region to be scanned is a two-dimensional region, the short-axis diameter is the distance connecting two points of intersection between a contour and a line perpendicular to the long axis at a pre-designated level along the long axis (e.g., a level at a position corresponding to ⅓ from the valve ring or each level in FIG. 3). Alternatively, the short-axis diameter is the maximum value of the distance connecting two points of intersection between a contour and a line perpendicular to the long axis at each level on the long axis.

When a region to be scanned is a three-dimensional region, the short-axis diameter D(t) is defined by methods (1) and (2) described next.

(1) A short-axis C-mode plane at a given long-axis level (h) is set at an initial phase. In this case, the short-axis C-mode plane means an arbitrary flat surface in the short-axis direction (including the short-axis direction). This short-axis C-mode plane is automatically set or manually and artificially set via the operation unit 41.

Figure 4:
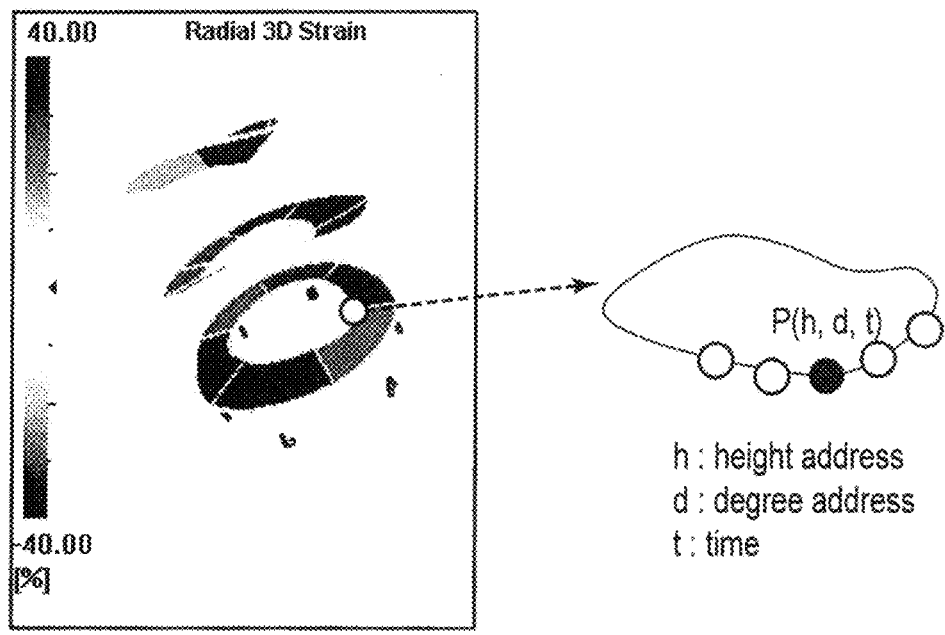
FIG. 4 is a view for explaining the relationship between a short-axis C-mode as curved surface and an apex P on a contour in three-dimensional speckle tracking processing.

The index value calculation unit 38 sets a short-axis C-mode as curved surface at each phase, for each point P(h, d, 0), of a tracking point group constituting a boundary surface of a tissue, which exists on a boundary line (outer circumference) of a short-axis C-mode plane set at an initial phase, by tracking a position (h, d, t) over the remaining phases using the result of tracking processing in step S2, as shown in FIG. 4. In this case, for each point on the boundary line, h represents an address in the height direction (long-axis direction), d represents an address in the circumferential direction (short-axis direction), and t represents an arbitrary phase.

The index value calculation unit 38 calculates the short-axis diameter D(t) at each phase by using one of techniques (a) to (c) described next using a short-axis C-mode as curved surface at each set phase.

Figure 5:
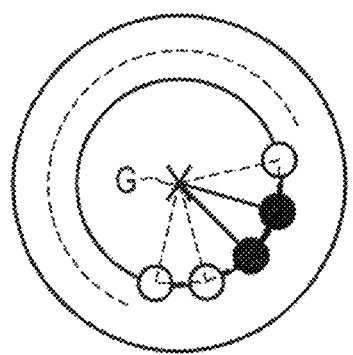
FIG. 5 is a schematic view for explaining a technique of calculating a short-axis diameter from a short-axis C-mode as curved surface in three-dimensional speckle tracking processing.

(a) In this technique, one short-axis diameter D(h, t) is acquired as a representative value from a short-axis C-mode as curved surface at a given long-axis level (h), and is shared at each point on the boundary line of the short-axis C-mode as curved surface. That is, as shown in FIG. 5, this technique calculates a barycentric position G as the average position of each point P (h, d, t) on the boundary line of the short-axis C-mode as curved surface set at each phase, and divides the short-axis C-mode as curved surface into a plurality of triangles each defined by the barycentric position G and two adjacent points on the boundary line. The area of each triangle is obtained from, for example, the lengths of the three sides according to a Heron's formula, and the total sum of the areas of all the triangles is calculated, thereby obtaining an area S(h) of the short-axis C-mode as curved surface at a level h. The technique calculates the short-axis diameter D(t) at each phase at the level h according to equation (1) assuming the obtained area S of the short-axis C-mode as curved surface and a circular shape:

$$D(h,T)=2(S(h)/\pi)^{1/2} \quad (1)$$

Figure 6:
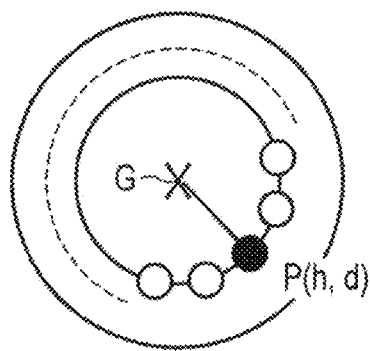
FIG. 6 is a schematic view for explaining a technique of calculating a short-axis diameter from a short-axis C-mode as curved surface in three-dimensional speckle tracking processing.

(b) This technique is designed to acquire a unique radius R(h, d, t) (or the diameter D(h, d, t) which is double the radius) at each point on a boundary line of a short-axis C-mode as curved surface. That is, as shown in FIG. 6, the distance connecting the barycentric position G and each point P(h, d, t) on a boundary surface is defined as the radius R(h, d, t) at the corresponding point, and the short-axis diameter D(t) at each position and each phase is calculated according to equation (2):

$$(D(h,d,t))=2R(h,d,t) \quad (2)$$

Figure 7:
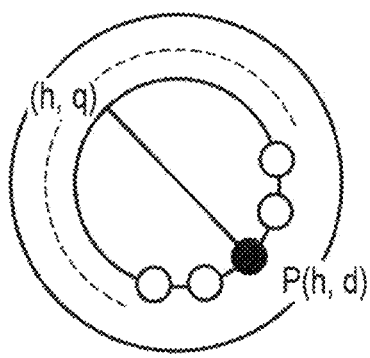
FIG. 7 is a schematic view for explaining a technique of calculating a short-axis diameter from a short-axis C-mode as curved surface in three-dimensional speckle tracking processing.

(c) This technique is designed to acquire the unique diameter D(h, d, t) at each point on a boundary line of a short-axis C-mode as curved surface. That is, as shown in FIG. 7, the distance from each point P(h, d, t) on a boundary surface at each phase to the furthest position within the short-axis C-mode as curved surface is calculated and defined as the short-axis diameter D(t) at each position.

It is possible to decide a short-axis diameter at each phase by selecting the short-axis diameter D(h, d, t) corresponding to a desired level along a predetermined long axis or the maximum value of the short-axis diameters D(h, d, t) at all long-axis levels by using the short-axis diameters D(h, d, t) obtained by either of the techniques (a) to (c) described above as in a case in which a region to be scanned is a two-dimensional region.

(2)) A plane (perpendicular to the long axis) with the long axis set at an arbitrary level (h) along the long axis being a normal line is set as a short-axis C-mode plane. Note that whether to set a short-axis C-mode plane at a specific level on the long axis is automatically or manually and artificially selected via the operation unit 41.

The index value calculation unit 38 calculates the short-axis diameter D(t) at each phase by using either of the techniques (a) to (c) using the set short-axis C-mode plane at each phase.

Each technique in method (1) described above directly estimates the short-axis diameter D(t) at each phase by using the position of each tracking point obtained by tracking processing. That is, in three-dimensional speckle tracking processing, the position of an arbitrary point P(h, d, t) moves while being tracked with time. It is therefore not guaranteed that the short-axis C-mode plane set at the initial phase is a flat surface at other phase. This surface generally becomes a curved surface. For example, in order to obtain the information of a short-axis diameter, positional information on the arbitrary point P(h, d, t) is used without any change and handled as each C-mode as curved surface.

Figure 8:
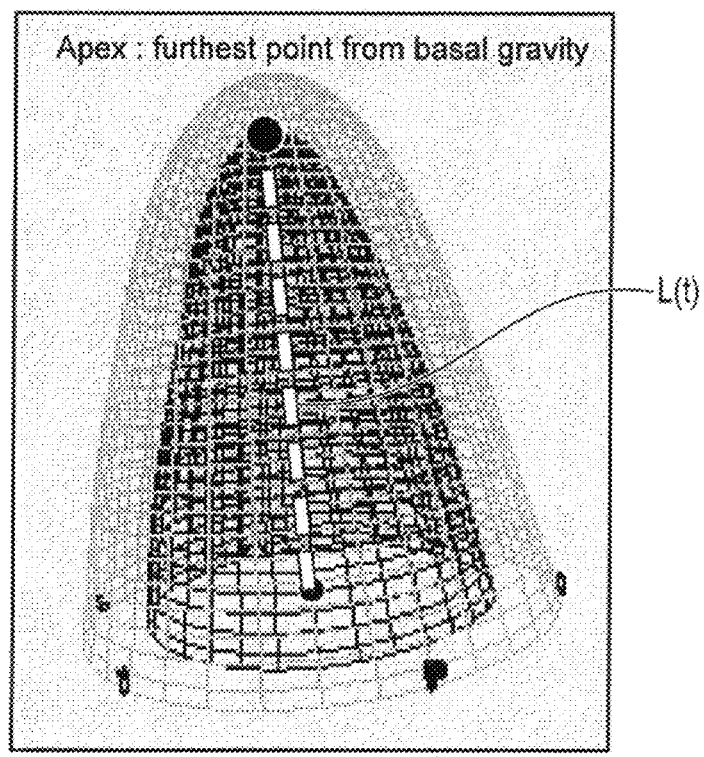
FIG. 8 is a schematic view for explaining a technique of calculating a long-axis length L(t) in three-dimensional speckle tracking processing and the relationship between a short-axis surface and an apex P on a contour.

Each technique in method (2) described above obtains each position on a boundary surface at each phase by spatially interpolating the tracking point obtained by tracking processing, and estimates the short-axis diameter D(t) at each phase from the result. That is, this technique obtains positional information about the boundary surface expressed by a mesh like that shown in FIG. 8 by interpolation from the position of each arbitrary point P(h, d, t). In this case, the technique sets an arbitrary short-axis level (h) relative to the long-axis length of a long axis L(h, d, t), defines, as a C-mode plane, a flat surface at the level (h) with a long axis being a normal vector, and obtains the position where the C-mode plane intersects the boundary by interpolation processing, thereby allowing to handle the C-mode plane as a flat surface.

[Calculation of Index Value: Step S4]

The index value calculation unit 38 calculates the long-axis length L(t), short-axis diameter D(t), and shape index value of the heart at each phase by using the long-axis length L(t) and short-axis diameter D(t) calculated in step S3 (step S4). If, for example, A=L/2 and B=D/2 (where L and D are a long-axis length and a short-axis length at a predetermined phase), eccentricity=$(A^2-B^2)^{1/2}/A$, flatness ratio=$(A-B)/A$, ellipticity=$B/A$, the like can be used.

[Output of Index Value: Step S5]

The acquired index value is displayed (output) in a predetermined form on the monitor of the display unit 23 (step S5). It is possible to use various kinds of display forms for index values. For example, the apparatus may display index values as numerical values together with an MPR image corresponding to each phase or may generate and display shape information including at least one of the difference value between an index value at an end-diastole and an index value at an end-systole, the ratio between an index value at an end-diastole and an index value at an end-systole, and an intra-cardiac cycle time change curve of an index value.

When using a maximum short-axis diameter maxD(d, h) as the short-axis diameter D(t) from diameters D(d, t) at all the levels, it is possible to use a display form that allows to easily and quickly comprehend, on an image, at which long-axis level (h) the short-axis diameter maxD(d, h) has been obtained. Typical examples of display forms include a form of displaying such information as a short-axis line segment in two-dimensional image display, a form of displaying such information as a C-mode surface using a short-axis C-mode as curved surface or short-axis C-mode plane in three-dimensional image display, a form of explicitly displaying a position on an ultrasonic image with a marker, a form of displaying such information together with positional information of the long-axis level (h) (e.g., information corresponding to a specific percentage of the long-axis length from the annulus) at which the short-axis diameter maxD(d, h) has been obtained, and a form of outputting such information as a numerical value to a file.

Figure 10:
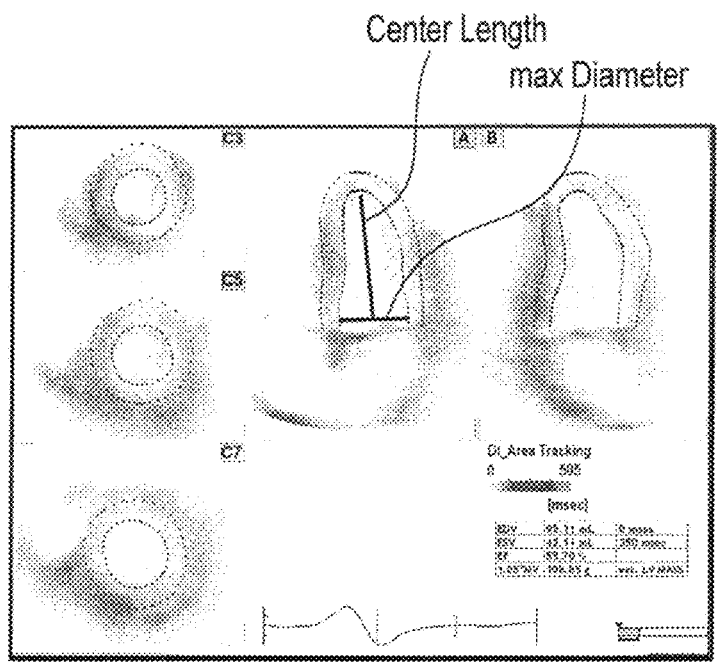
FIG. 10 is a view showing an MPR image at an end-systolic phase (ES) of a normal subject.
Figure 11:
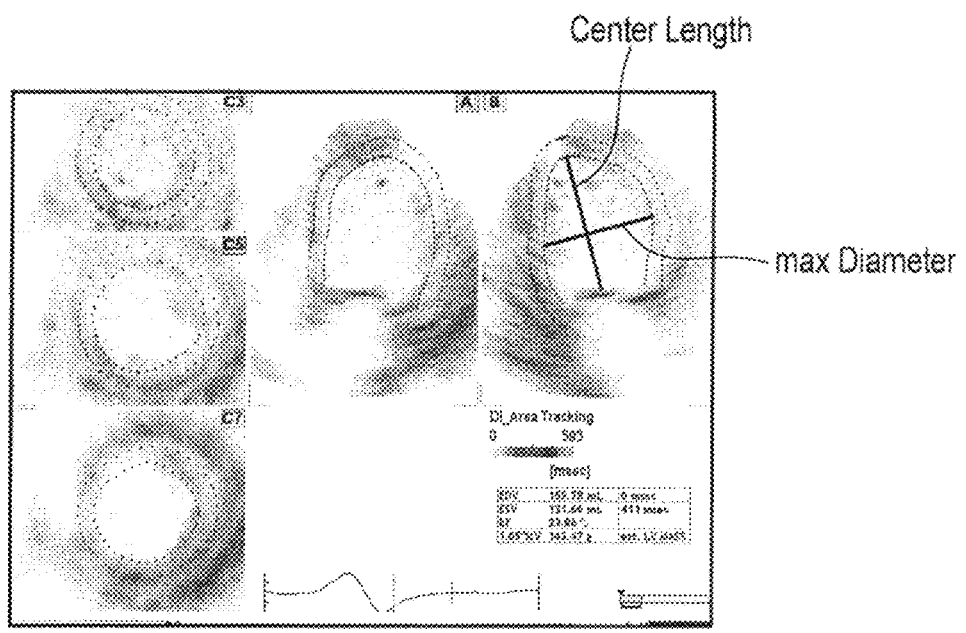
FIG. 11 is a view showing an MPR image at an end-systolic phase (ES) of a DCM patient.

FIG. 9 is a graph showing the intra-cardiac cycle time change curve of the eccentricity obtained by this shape information calculation processing with a region to be scanned being a three-dimensional region, which is generated for each of a normal subject and a DCM patient. FIG. 10 is a view showing an MPR image at an end-systolic phase (ES) of a normal subject. FIG. 11 is a view showing an MPR image at an end-systolic phase (ES) of a DCM patient. Each of FIGS. 10 and 11 shows a case in which the short-axis diameter D(t) is defined by the maximum value of the diameters obtained as representative values from the areas of all the C-mode surfaces (short-axis C-mode as curved surfaces or short-axis C-mode plane) by circle approximation. In MPR image display in FIGS. 10 and 11, the positions of a long axis (CenterLength) and maximum short-axis diameter (max_Diameter) are displayed by line segments. It is possible to display simultaneously or selectively the time change curves shown in FIG. 9 and the MPR images displayed in FIGS. 10 and 11.

Referring to the time change curve of FIG. 9, the normal case having an elongated shape with the long-axis length being larger than the maximum short-axis diameter indicates that the value of eccentricity is larger than the DCM patient with a shape closer to a circle as a whole throughout a cardiac phase. In addition, it is possible to recognize, from this time change curve, that the eccentricity of the normal case exhibits an increasing tendency (↑) more at an end-diastole than at an end-systole, whereas the eccentricity of the DCM patient exhibits a decreasing tendency (↓). A contributing factor may be that in the normal case, the maximum short-axis diameter has decreased relative to the long-axis length due to twisting motion at an end-systole or a circumferential strain (CS) correlated with the change ratio of short-axis diameter and a longitudinal strain (LS) correlated with the change ratio of long-axis length hold |CS|>|LS| (it is known that CS is about −30% and LS is about −20% in the normal case).

In contrast, it is thought that in the DCM patient, the elasticity (Emax) at an end-systole which is correlated with the contractile ability of myocardium has decreased, and the shape of the left ventricle has been swollen and rounded more by being pressed by the left ventricular end-systolic pressure (blood pressure).

Figure 12:
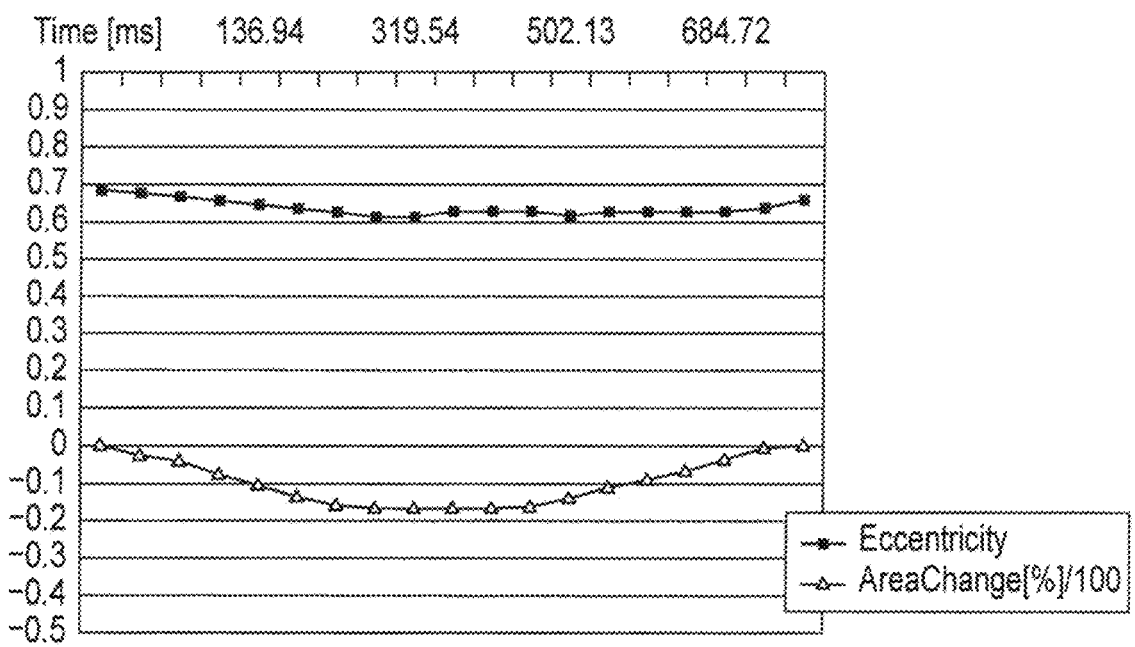
FIG. 12 is a graph showing an example of the time change curves of eccentricity and area change ratio of endocardium which are generated for a DCM patient and obtained by shape information calculation processing targeted at a three-dimensional region as a region to be scanned.
Figure 13:
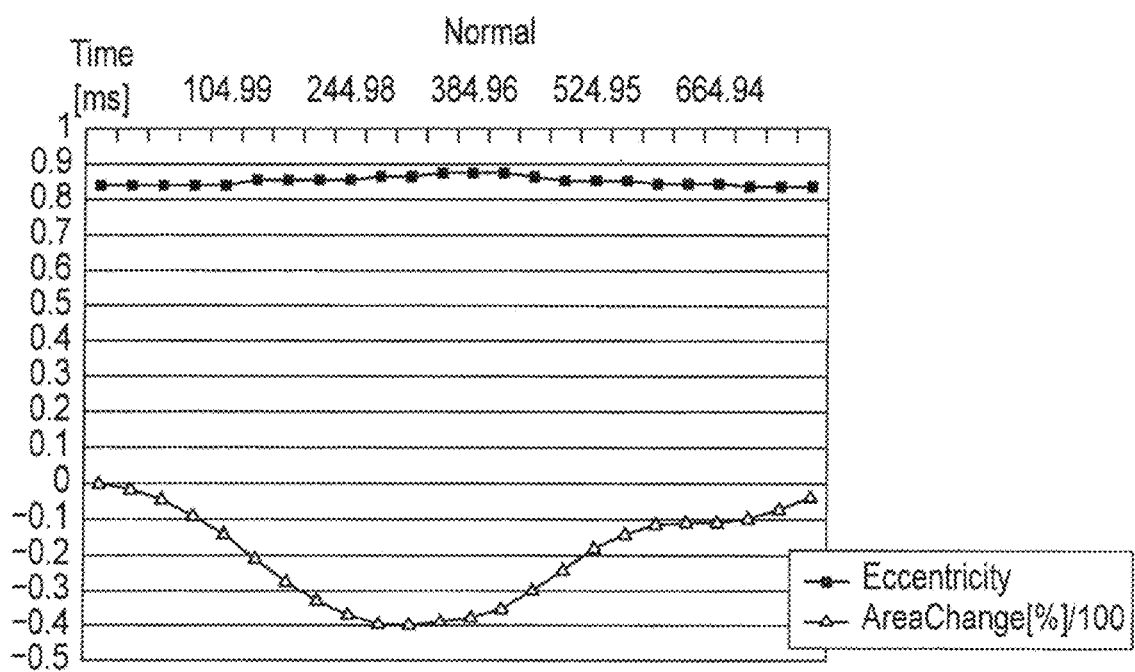
FIG. 13 is a graph showing an example of the time change curves of eccentricity and area change ratio of endocardium which are generated for a normal subject and obtained by shape information calculation processing targeted at a three-dimensional region as a region to be scanned.

It is also possible to simultaneously display index values indicating a shape and wall motion information. FIGS. 12 and 13 each are a graph showing an example of the time change curves of eccentricity and area change ratio of endocardium which are generated for each of a DCM patient and a normal subject and obtained by shape information calculation processing targeted at a three-dimensional region as a region to be scanned. The respective curves shown in FIGS. 12 and 13 may be simultaneously or selectively displayed. Note that the area change ratio of endocardium due to three-dimensional tracking is disclosed in detail in a known literature by the present inventors (Jpn. Pat. Appln. KOKAI Publication No. 2010-274673). Referring to FIGS. 12 and 13, the area change ratios [%] are expressed by values divided by 100.

First Modification

When performing shape assessment of the left ventricle, left atrium, and right atrium, since each shape is close to a spheroid, it is possible to perform shape assessment even by technique (a) described above based on circle approximation. On the other hand, in the case of the right ventricle having a complicated shape, it is preferable to define local short-axis diameters such as a long diameter α(h) and short diameter β(h) concerning D(h) by using the examples of (b) and (c) within a short-axis C-mode surface at each long-axis level (h) and assess detailed shape information.

Figure 14:
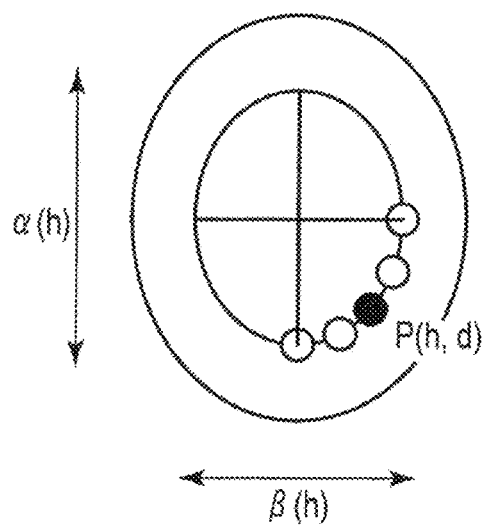
FIG. 14 is a schematic view for explaining a modification of obtaining the detailed information of a short-axis diameter from a short-axis C-mode as curved surface in three-dimensional speckle tracking processing.

The long diameter α(h) and the short diameter β(h) may be statistical information such as the maximum value and minimum value of the respective diameters D(h, d, t), or may be obtained by assuming an elliptic shape like that shown in FIG. 14. As indicated by technique (a), the area S(h) of a C-mode surface is obtained, and a diameter x (h) which is either the long diameter or the short diameter of an ellipse concerning the C-mode surface is defined by the maximum value or minimum value of D(h, d, t), thereby estimating the other diameter y(h) according to y(h)=S(h)/(π×x(h)). It is also possible to assess detailed shape information by using statistical information such as a variance and standard deviation among apexes of D(h, d, t) at the respective apexes on the same C-mode surface. Obviously, it is possible to assess the shape of the left ventricle as well as the right ventricle by using such detailed shape information.

Second Modification

In the above embodiment, the apparatus executes tracking processing by using, for example, image data corresponding to each phase in one heartbeat (at all phases), and acquires the positional information of a tissue in a region of interest at each phase, thereby executing the above shape information calculation function. However, it is possible to execute tracking processing by using image data corresponding to a desired phase (e.g., an end-diastole or end-systole) or a desired period (an end-diastolic period or end-systolic period), acquire the positional information of a tissue in a region of interest at all phases, and acquire shape indices corresponding to desired phases and periods, as needed.

In the above embodiment, the apparatus has executed tracking processing by using image data throughout a period of one or more heartbeats, and has executed the shape information calculation function by using the processing result. However, the apparatus may be configured to execute tracking processing by using image data throughout a predetermined period (e.g., a period of several hundred ms equal to or less than one heartbeat) instead of a cardiac cycle and execute the above shape information calculation function by using the processing result. This arrangement is useful, for example, for a case in which it is difficult to comprehend an accurate cardiac cycle as in the case of the heart of a fetus, a case in which it is not necessary to limit this technique to a cardiac cycle as in the case of a hepatic tumor, and a case in which it is possible to sufficiently acquire shape information even in a period equal or less than one heartbeat.

Third Modification

Figure 15:
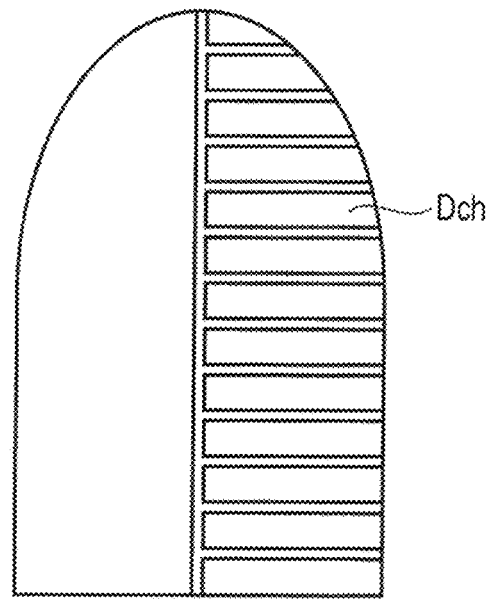
FIG. 15 is a view for explaining a modification of calculating and displaying the statistical information of local short-axis diameters as a shape index value.

For the long-axis slice as shown in FIG. 15, for example, the apparatus may calculate the local short-axis axis D(h) at each depth (each long-axis level h) from the deepest portion to the shallowest portion of the long axis, calculate a predetermined statistical amount (e.g., at leas one of the average value, maximum value, minimum value, median value, or standard deviation of the local short-axis diameters D(h)) by using the plurality of obtained local short-axis diameters D(h), and display the calculated amounts as shape index values. In addition, when, for example, a region to be scanned is a three-dimensional region, the apparatus may calculate long-axis lengths and local short-axis diameters D(h) at the respective depths from the deepest portion to the shallowest portion of the long axis by the above technique, calculate predetermined statistical amounts in the same manner as described above, and display the calculated amounts as shape index values. This arrangement allows to easily and quickly recognize distribution information such as variations in local short-axis diameter D(h).

Fourth Modification

The above embodiment has exemplified the case in which the shape information calculation function is implemented by using the ultrasonic image data acquired by the ultrasonic diagnostic apparatus. It is possible to implement the above shape information calculation function by using the image data acquired by an X-ray computed tomography apparatus and a magnetic resonance imaging apparatus. This shape information calculation function is not limited to the case in which it is implemented in various kinds of modalities such as an ultrasonic diagnostic apparatus, X-ray computed tomography apparatus, and magnetic resonance imaging apparatus, and may be configured to be implemented in a medical image processing apparatus (medical workstation).

The above ultrasonic diagnostic apparatus automatically calculates shape information (direct information concerning a shape, e.g., the long-axis length L and the short-axis diameter D of a diagnostic target or index values (shape index values) reflecting the shape of a moving tissue which are obtained by using the long-axis length L and short-axis diameter D of a diagnostic target) by using the positional information of the tissue obtained by tracking processing throughout at least one cardiac cycle, and outputs the index values in a predetermined form. This makes it possible to easily and quickly quantify the shape information of the heart at an arbitrary phase. In addition, it is possible to provide a new disease condition assessment method using a time change in shape information such as eccentricity throughout one cardiac cycle.

The shape index calculation processing based on three-dimensional speckle tracking processing allows to uniquely determined shape information with ease and stability. It is therefore possible to acquire shape information reflecting the entire cardiac region at a time with high reproducibility, reduce uncertainties in image diagnosis, and improve shape assessment as compared shape index calculation processing based on two-dimensional tracking processing.

In addition, it is possible to display the index values obtained by shape index calculation processing, together with wall motion information in a predetermined form. Therefore, the observer can perform image diagnosis using index values indicating a shape and wall motion information without being imposed by any special load. This can contribute to an improvement in image diagnosis quality.

Note that the present invention is not limited to each embodiment described above, and constituent elements can be modified and embodied in the execution stage within the spirit and scope of the invention. In addition, various inventions can be formed by proper combinations of a plurality of constituent elements disclosed in the above embodiments. For example, several constituent elements may be omitted from all the constituent elements disclosed in the above embodiments. Furthermore, constituent elements in different embodiments may be properly combined.

The invention claimed is:

1. An ultrasonic diagnostic apparatus, comprising:
a data acquisition unit configured to execute ultrasonic scanning, via an ultrasonic probe, of a tissue throughout a predetermined period and acquire a plurality of image data respectively corresponding to phases in the predetermined period; and
processing circuitry configured to
acquire a surface in a short-axis direction in first image data at a first phase of the plurality of image data in the period;
set the surface in second image data at a second phase of the plurality of image data in the period by executing tracking processing using the second image data, at the second phase, of the plurality of image data, wherein the tracking processing tracks the surface acquired at the first phase from the first phase to the second phase;
calculate a respective short-axis diameter of the tissue from the surface set at the second phase by the tracking processing for each of plural positions along a long-axis direction;
select, from among the plural respective calculated short-axis diameters, a maximum short-axis diameter that is a diameter that has the largest either area or diameter in a plurality of planes defined along the long-axis length;
calculate an index value representing a shape of the tissue at the second phase by using a long-axis length and the maximum short-axis diameter of the tissue; and output the index value.

2. The ultrasonic diagnostic apparatus of claim 1, wherein the tissue periodically varies, and
the processing circuitry is further configured to execute the tracking processing throughout a period of at least one cycle of the periodic variation.

3. The ultrasonic diagnostic apparatus of claim 1, wherein the tissue periodically varies, and the processing circuitry is further configured to execute the tracking processing throughout a period of less than at least one cycle of the periodic variation.

4. The ultrasonic diagnostic apparatus of claim 1, wherein the processing circuitry is further configured to calculate motion information of the tissue at at least one phase in the period by using the surface at the at least one phase, and
wherein the processing circuitry is further configured to cause a display to simultaneously display the index value and the motion information at the at least one phase.

5. The ultrasonic diagnostic apparatus of claim 1, wherein the tissue includes the heart, and
the processing circuitry is further configured to acquire the surface in the tissue at at least an end diastolic phase and an end systolic phase, and calculate the index value at at least an end diastolic phase and an end systolic phase.

6. The ultrasonic diagnostic apparatus of claim 1, wherein the processing circuitry is further configured to generate, as shape change information, one of a difference value between the index value at an end diastole and the index value at an end systole and a ratio between the index value at an end diastole and the index value at an end systole, and
the display displays the shape change information together with the index value or instead of the index value.

7. The ultrasonic diagnostic apparatus of claim 1, wherein when the tissue region includes the heart, and the processing circuitry is further configured to calculate the long axis length by using an average position of a basal annulus portion and an average position of a cardiac apex of a portion in one of four atriums and ventricles of the heart.

8. The ultrasonic diagnostic apparatus of claim 1, wherein the data acquisition unit acquires, via the ultrasonic probe, the plurality of image data by executing the ultrasonic scanning for a three dimensional region as the tissue region, and
the processing circuitry is further configured to acquire the surface in the tissue at at least one phase in the period by executing three-dimensional tracking processing.

9. The ultrasonic diagnostic apparatus of claim 1, wherein the processing circuitry is further configured to calculate, as the index value, statistical information including at least one of an average value, maximum value, minimum value, median value, and standard deviation of the local diameters calculated for the surface.

10. The ultrasonic diagnostic apparatus of claim 1, wherein the processing circuitry is further configured to calculate the maximum short axis diameter by using a distance between each position on a contour of the surface set in the short axis direction and a furthest point on the contour.

11. The ultrasonic diagnostic apparatus of claim 1, wherein the display displays information concerning a position as a reference for calculation of the maximum short axis diameter together with the index value.

12. The ultrasonic diagnostic apparatus according to claim 1, wherein the long-axis length is calculated using the first image data at the first phase.

13. The ultrasonic diagnostic apparatus according to claim 1, wherein the long-axis length is determined by anatomical landmarks.

14. The ultrasonic diagnostic apparatus according to claim 1, wherein the long-axis length is determined as a distance between a cardiac apex position and a middle point of a straight line connecting an edge of basal myocardium on an apical view at the first phase.

15. The ultrasonic diagnostic apparatus according to claim 1, wherein the long-axis length is determined as a distance between a cardiac apex position and a barycenter of a short-axis C-mode as curved surface of the edge of a basal level of the first image data or the second image data level.

16. A medical image processing apparatus, comprising:
a memory to store a plurality of image data respectively corresponding to phases in a predetermined period, wherein the image data have been obtained by capturing a tissue throughout the predetermined period;
processing circuitry configured to
acquire a surface in a short-axis direction in first image data at a first phase of the plurality of image data in the period,
set the surface in second image data at a second phase of the plurality of image data in the period by executing tracking processing using the second image data, at the second phase, of the plurality of image data;
calculate a respective short-axis diameter of the tissue from the surface set at the second phase by the tracking processing for each of plural positions along a long-axis direction;
select, from among the plural respective calculated short-axis diameters, a maximum short-axis diameter that is a diameter that has the largest either area or diameter in a plurality of planes defined along the long-axis length;
calculate an index value representing a shape of the tissue at the second phase by using a long-axis length and the maximum short-axis diameter of the tissue; and output the index value.

17. A medical image processing method, comprising:
acquiring a plurality of image data respectively corresponding to phases in a predetermined period which have been obtained by capturing a tissue throughout the predetermined period;
acquiring a surface in a short-axis direction in first image data at a first phase of the plurality of image data in the period,
setting the surface in second image data at a second phase of the plurality of image data in the period by executing tracking processing using the second image data, at the second phase, of the plurality of image data;
calculating a respective short-axis diameter of the tissue from the surface set at the second phase by the tracking processing for each of plural positions along a long-axis direction;
selecting, from among the plural respective calculated short-axis diameters, a maximum short-axis diameter that is a diameter that has the largest either area or diameter in a plurality of planes defined along the long-axis length;
calculate an index value representing a shape of the tissue at the second phase by using a long-axis length and the maximum short-axis diameter of the tissue; and output the index value.

18. An ultrasonic diagnostic apparatus, comprising:
a data acquisition unit configured to execute ultrasonic scanning, via an ultrasonic probe, of a tissue throughout a predetermined period and acquire a plurality of image data respectively corresponding to phases in the predetermined period;
processing circuitry configured to
acquire a surface in a short-axis direction in first image data at a first phase of the plurality of image data in the period,
set the surface in second image data at a second phase of the plurality of image data in the period by executing tracking processing using the second image data, at the second phase, of the plurality of image data; and
calculate a representative maximum short-axis diameter of the tissue from the surface set at the second phase by the tracking processing for each of plural positions along a long-axis direction;
select, from among the plural respective calculated short-axis diameters, a maximum short-axis diameter that is a diameter that has the largest either area or diameter in a plurality of planes defined along the long-axis length;

calculate an index value representing a shape of the tissue at the second phase by using a long-axis length and the representative maximum short-axis diameter of the tissue; and output the index value.

* * * * *